United States Patent [19]

Hoffmann et al.

[11] 4,034,085

[45] July 5, 1977

[54] O-[1-ALKOXYPHOSPHORYL-3-METHYL-PYRAZOL(5)YL]-(THIONO)PHOSPHORIC ACID ESTERS AND ESTER AMIDES

[75] Inventors: Hellmut Hoffmann, Wuppertal; Ingeborg Hammann, Cologne, both of Germany

[73] Assignee: Bayer Aktiengesellschaft, Leverkusen, Germany

[22] Filed: Oct. 21, 1976

[21] Appl. No.: 734,480

[30] Foreign Application Priority Data

Oct. 28, 1975 Germany ............ 2548183

[52] U.S. Cl. ............ 424/200; 260/310 R; 424/273

[51] Int. Cl.[2] ........ A01N 9/36; C07F 9/65

[58] Field of Search ........ 260/310 R; 424/200, 424/273

[56] References Cited

UNITED STATES PATENTS

| | | | |
|---|---|---|---|
| 3,010,969 | 11/1961 | Rogterink | 260/310 R |
| 3,700,686 | 10/1972 | Fest et al. | 260/310 R |
| 3,700,687 | 10/1972 | Hoffmann et al. | 260/310 R |
| 3,723,456 | 3/1973 | Fest et al. | 260/310 R |

*Primary Examiner*—Donald B. Moyer

*Attorney, Agent, or Firm*—Burgess, Dinklage & Sprung

[57] ABSTRACT

O-[1-Alkoxyphosphoryl-3-methyl-pyrazol(5)yl]-(thiono)phosphoric acid esters and ester amides of the formula

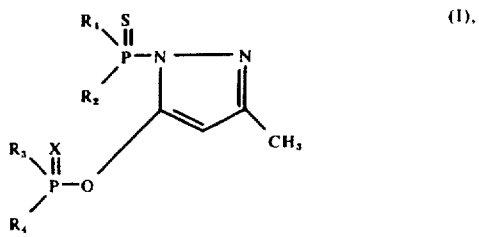

(I).

in which $R_1$ is alkoxy with 1 to 4 carbon atoms, $R_2$ and $R_3$ each independently is alkoxy or alkylthio with 1 to 6 carbon atoms, $R_4$ is alkoxy, alkylthio, alkylamino or alkyl with 1 to 5 carbon atoms, provided that at least one of the radicals $R_2$, $R_3$ and $R_4$ is alkylthio, and X is oxygen or sulfur, which possess arthropodicidal properties.

10 Claims, No Drawings

O-[1-ALKOXYPHOSPHORYL-3-METHYL-PYRAZOL(5)YL]-(THIONO)PHOSPHORIC ACID ESTERS AND ESTER AMIDES

The present invention relates to and has for its objects the provision of particular new O-[1-alkoxyphosphoryl-3-methyl-pyrazol(5)yl]-(thiono)phosphoric acid esters and ester amides which possess arthropodicidal properties, active compositions in the form of mixtures of such compounds with solid and liquid dispersible carrier vehicles, and methods for producing such compounds and for using such compounds in a new way especially for combating pests, e.g. arthropods, with other and further objects becoming apparent from a study of the within specification and accompanying examples.

It is known from German Published Specification DOS 1,917,741 that diphosphorylated pyrazoles, for example O,O-dimethyl(Compound A) and O,O-diethyl-O-[3-methyl-1-dimethoxythionophosphoryl-pyrazol(5)yl]-phosphoric acid ester (Compound B) and -thionophosphoric acid esters (Compounds C and D, respectively) and O-ethyl-O-O-[3-methyl-1-dimethoxythionophosphorylpyrazol(5)yl]-ethane- (Compound E) and O-ethyl-O-[3-methyl-1-diethoxythionophosphoryl-pyrazol(5)yl]-benzene-thionophosphonic acid esters (Compound F), possess insecticidal and acaricidal properties.

The present invention provides, as new compounds, the diphosphorylated pyrazoles of the general formula

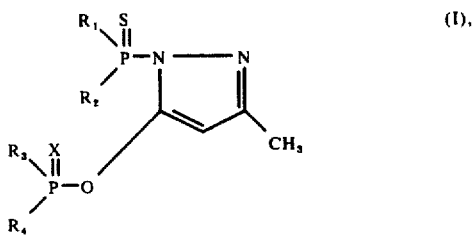

in which
R₁ is alkoxy with 1 to 4 carbon atoms,
R₂ and R₃ each independently is alkoxy or alkylthio with 1 to 6 carbon atoms,
R₄ is alkoxy, alkylthio, alkylamino or alkyl with 1 to 5 carbon atoms, provided that at least one of the radicals R₂, R₃ and R₄ is alkylthio, and
X is oxygen or sulfur.

Preferably, R₁ represents straight-chain or branched alkoxy with 1 to 3 carbon atoms, R₂ represents straight-chain or branched alkoxy with 1 to 3 carbon atoms, or alkylthio with 1 to 4 carbon atoms, R₃ represents straight-chain or branched alkoxy with 1 to 3 carbon atoms or alkylthio with 1 to 5 carbon atoms, R₄ represents straight chain or branched alkyl with 1 to 3 carbon atoms or alkoxy, alkylthio or alkylamino, each with 1 to 4 carbon atoms, provided that at least one of the radicals R₂ to R₄ represents alkylthio (especially n-propylthio), and X represents sulfur.

Surprisingly, the diphosphorylated pyrazoles according to the invention have a better insecticidal and acaricidal action than the corresponding known active compounds of similar structure and of the same type of action. The products according to the present invention thus represent a genuine enrichment of the art.

The present invention also provides a process for the preparation of a diphosphorylated pyrazole of the formula (I) in which an alkali metal salt of a monophosphorylated pyrazole of the general formula

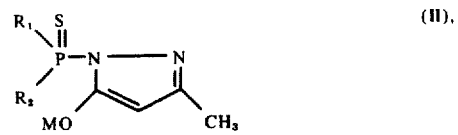

in which
R₁ and R₂ have the above-mentioned meanings and
M represents an alkali metal, preferably sodium,
is reacted with a (thiono) (thiol)phosphoric(phosphonic) acid ester halide or ester-amide halide of the general formula

wherein
R₃, R₄ and X have the above-mentioned meanings and
Hal represents halogen, preferably chlorine,
if appropriate in the presence of a diluent or solvent.

If, for example, O-ethyl-S-n-propylthionothiolphosphoric acid ester chloride and the sodium salt of 1-diethoxythionophosphoryl-3-methyl-5-hydroxy-pyrazole are used as starting materials, the course of the reaction can be represented by the following equation:

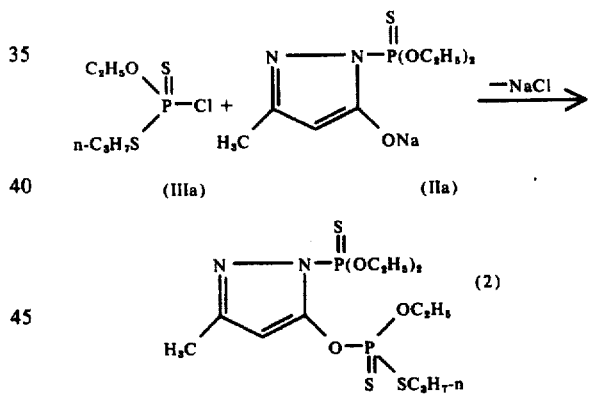

The (thiono)(thiol)phosphoric(phosphonic) acid ester halides and ester-amide halides (III) to be used as starting materials are known and can be prepared in accordance with customary processes.

The following may be mentioned as individual examples: O,O-dimethyl-, O,O-diethyl-, O,O-dipropyl-, O,O-diisopropyl-, O,O-dibutyl-, O,O-di-sec.-butyl-, O-methyl-O-ethyl- and O-ethylO-N-propyl-phosphoric acid diester chlorides and the corresponding thiono analogues; O,S-dimethyl-, O,S-diethyl-, O,S-di-n-propyl-, O,S-di-isopropyl-, O,S-di-n-butyl-, O,S-diisobutyl-, O,S-di-tert.-butyl-, O,S,-di-n-pentyl-, O-ethyl-S-n-propyl-, O-ethyl-S-isopropyl-, O-ethyl-S-n-butyl-, O-ethyl-S-sec.-butyl-, O-n-propyl-S-ethyl-, O-n-propyl-S-isopropyl-, O-n-butyl-S-n-propyl- and O-sec.-butyl-S-ethyl-thiolphosphoric acid diester halides and the corresponding thiono analogues; O-methyl-, O-ethyl-, O-n-propyl-, O-isopropyl-, O-n-butyl-, O-isobutyl-, O-sec.-butyl-, O-tert.-butyl- and O-n-pentylmethane-, -ethane- , -n-propane-, -isopropane-, -n-butane-, -iso-butane-, -tert.-butane- and -sec.-butane-phosphonic acid ester halides and the corresponding thiono analogues; S,S-dimethyl-, S,S-diethyl-, S,S -di-n-propyl-, S,S -diisopropyl- and S,S-dibutyl-dithiolphosphoric acid diester halides and the corresponding thiono analogues; and O-methyl-N-methyl-, O-methyl-N-ethyl-, O-methyl-N-n-propyl-, O-methyl-N-isopropyl-, O-ethyl-N-methyl-, O-ethyl-N-ethyl-, O-ethyl-N-n-propyl-, O-ethyl-N-isopropyl-, O-n-propyl-N-methyl-, O-n-propyl-N-ethyl-, O-n-propyl-N-n-propyl-, O-n-propyl-N-isopropyl-, O-isopropyl-N-methyl-, O-isopropyl-N-ethyl-, O-isopropyl-N-n-propyl-, O-isopropyl-N-isopropyl-, O-n-butyl-N-methyl-, O-n-butyl-N-ethyl-, O-n-butyl-N-n-propyl-, O-n-butyl-N-isopropyl-, O-tert.-butyl-N-methyl-, O-tert.-butyl-N-ethyl-, O-tert.-butyl-N-n-propyl-, O-tert.-butyl-N-isopropyl-, O-isobutyl-N-methyl-, O-isobutyl-N-ethyl-, O-sec.-butyl-N-methyl- and O-sec.-butyl-N-ethyl-phosphoric acid ester-amide halides and the corresponding thiono analogues.

Alkali metal salts of the substituted pyrazoles (II), which are also to be used as starting materials, have been described and are preparable in accordance with processes known from the literature, e.g. German Published Specification DOS 1,917,741, for example by reacting thionophosphoric acid ester halides with hydrazine hydrate to give the phosphorylated hydrazide and reacting this further with an acetoacetic acid ester to give the corresponding phosphorylated hydrazonocarboxylic acid ester derivative, which is cyclized by the action of alkali metal alcholates.

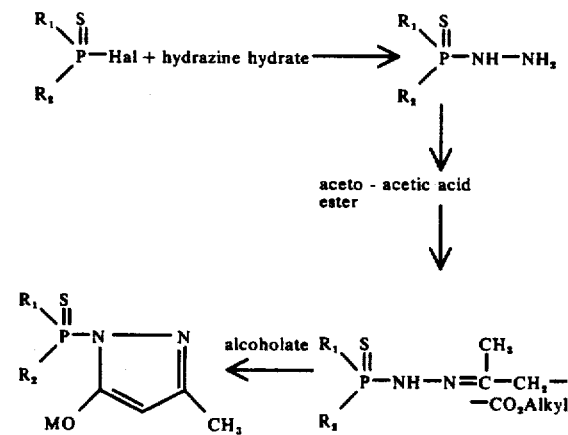

In the above reaction scheme, $R_1$, $R_2$, Hal and M have the above-mentioned meanings and Alkyl denotes lower alkyl.

The following may be mentioned as individual examples of pyrazole salts (II) to be reacted in accordance with the process: the alkali metal salts, preferably the sodium salts, of 1-(dimethyloxy-thionophosphoryl)-, 1-(diethoxythionophosphoryl)-, 1-(di-n-propoxythionophosphoryl)-, 1-(diisopropoxythionophosphoryl)-, 1-(methoxy-methylthio-thionophosphoryl)-, 1-(ethoxy-ethylthio-thionophosphoryl)-, 1-(ethoxy-n-propylthiothionophosphoryl)-, 1-(ethoxy-isopropylthio-thionophosphoryl)-, 1-(n-propoxy-ethylthiothionophosphoryl)- and 1-(isopropoxy-ethylthiothionophosphoryl)-3-methyl-5-hydroxy-pyrazole.

All inert organic solvents, or their mixtures, can be used as solvents or diluents for the reaction. Aliphatic and aromatic hydrocarbons, for example benzene, benzine, toluene and xylene, ethers, such as diethyl ether, dibutyl ether and dioxane, and ketones, for example acetone, methyl ethyl ketone, methyl isopropyl ketone and methyl isobutyl ketone, are particularly suitable.

The reaction temperatures can be varied within a fairly wide range. In general, the reaction is carried out at between 0° and 100° C, preferably at from 40° to 70° C.

The reaction is in general allowed to take place under normal pressure.

In carrying out the process, the starting materials are preferably employed in equimolar amounts. The reaction is carried out in the usual manner by bringing the reactants together in one of the above-mentioned solvents or diluents. After stirring the mixture for several hours at elevated temperature, the mixture is cooled, poured into water and extracted by shaking with an organic solvent, for example methylene chloride, and the solvent is then distilled off, after washing and drying.

The diphosphorylated pyrazoles according to the invention are obtained in the form of colorless to pale yellow-colored oils, which cannot be distilled without decomposition; however, they can be freed from the last volatile constituents by so-called "slight distillation", that is to say prolonged heating under reduced pressure to moderately elevated temperatures, and can be purified in this way. They are characterized, above all, by the refractive index.

As already mentioned, the compounds according to the present invention are distinguished by an excellent insecticidal and acaricidal activity. They act against plant pests, pests harmful to health and pests of stored products. They have a low phytotoxicity and a good action against both sucking and biting insects and against mites.

For this reason, the compounds according to the invention can be employed successfully as pesticides in plant protection and in the hygiene field and the field of protection of stored products.

The active compounds are well tolerated by plants, have a favorable level of toxicity to warm-blooded animals, and can be used for combating arthropod pests, espcially insects and arachnids which are encountered in agriculture, in forestry, in the protection of stored products and of materials, and in the hygiene field. They are active against normally sensitive and resistant species and against all or some stages of development.

The above-mentioned pests include: from the class of the Isopoda, for example *Oniscus asellus*, *Armadillidium vulgare* and *Porcellio scaber*; from the class of the Diplopoda, for example *Blaniulus guttulatus*; from the class of the Chilopoda, for example *Geophilus carpophagus* and *Scutigera* spec.; from the class of the Symphyla, for example *Scutigerella immaculata*; from the class of the Thysanura, for example *Lepisma saccharina*; from the class of the Collembola, for example *Onychiurus armatus*; from the class of the Orthoptera, for example *Blatta orientalis*, *Periplaneta americana*, *Leucophaea maderae*, *Blattella germanica*, *Acheta domesticus*, *Gryllotalpa* spp., *Locusta migratoria migratorioides*, *Melanoplus differentialis* and *Schistocerca gregaria*; from the class of the Dermaptera, for example *Forficula auricularia*; from the class of the Isoptera, for example *Reticulitermes* spp.; from the class of the Anoplura, for example *Phylloxera vastatrix*, Pemphigus spp., *Pediculus humanus corporis*, Haematopinus spp. and Linognathus spp.; from the class of the Mallophaga, for example Trichodectes spp. and Damalinea spp.; from the class of the Thysanoptera, for example *Hercinothrips femoralis* and *Thrips tabaci*; from the class of the Heteroptera, for example Eurygaster spp., *Dysdercus intermedius, Piesma quadrata, Cimex lectularius, Rhodnius prolixus* and Triatoma spp.; from the class of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.; from the class of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia keuhniella, Galleria mellonella, Cacoecia podana, Capua reticulana, Choristoneura fumiferana, Clysia ambiguella, Homona magnanima* and *Tortrix viridana;* from the class of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., Oryzaephilus surinamensis, Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psyllloides,* Tribolium spp., *Tenebrio molitor,* Agriotes spp., Conoderus spp., Melolontha melolontha, Amphimallon solstitialis and *Costelytra zealandica;* from the class of the Hymenoptera, for example, Diprion spp., Hoplocampa spp., Lasius spp., Monomorium pharaonis and Vespa spp.; from the class of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp, Hypoderma spp., Tabanus spp., Tannia spp., *Bibio hortulanus, Oscinella frit,* Phorbia spp., *Pegomyia hyoscyami, Geratitis capitata, Dacus oleae* and *Tipula paludosa;* from the class of the Siphonaptera, for example *Xenopsylla cheopis* and Ceratophyllus spp.; from the class of the Arachnida, for example *Scorpio maurus* and *Latrodectus mactans;* from the class of the Acarina, for example *Acarus sior,* Argas spp., Ornithodorus spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., and Tetranychus spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, forms, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other insecticides and acaricides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.1–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods such as insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 1
(insects which damage plants)
(*Plutella* test)
| Active compounds | Active compound concentration in % | Degree of destruction in % after 3 days |
|---|---|---|
| 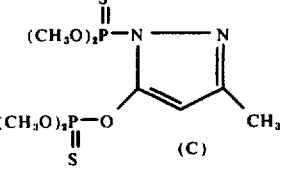 (C) (known) | 0.1<br>0.01<br>0.001 | 100<br>100<br>0 |
| 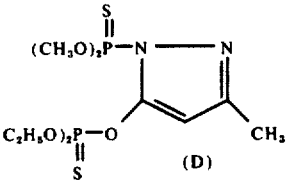 (D) (known) | 0.1<br>0.01<br>0.001 | 100<br>30<br>0 |
| 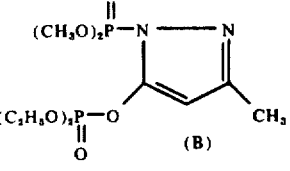 (B) (known) | 0.1<br>0.01<br>0.001 | 100<br>100<br>0 |
| 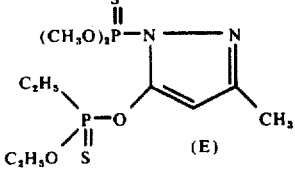 (E) (known) | 0.1<br>0.01<br>0.001 | 100<br>85<br>0 |
| 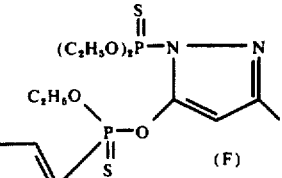 (F) (known) | 0.1<br>0.01<br>0.001 | 100<br>100<br>0 |
| 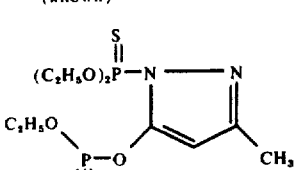 (2) | 0.1<br>0.01<br>0.001 | 100<br>100<br>100 |
| 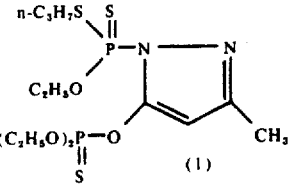 (1) | 0.1<br>0.01<br>0.001 | 100<br>100<br>90 |

Table 1-continued (insects which damage plants)
(*Plutella* test)

| Active compounds | Active compound concentration in % | Degree of destruction in % after 3 days |
|---|---|---|
| (13) n-C$_3$H$_7$S, C$_2$H$_5$O-P(S)-N... ; C$_2$H$_5$O, C$_2$H$_5$S-P(S)-O-... CH$_3$ | 0.1<br>0.01<br>0.001 | 100<br>100<br>100 |

EXAMPLE 2

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 2

(insects which damage plants)
(*Myzus* test)

| Active compounds | Active compound concentration in % | Degree of destruction in % after 1 day |
|---|---|---|
| (F) (C$_2$H$_5$O)$_2$P(S)-N...; C$_2$H$_5$O, C$_6$H$_5$-P(S)-O-... CH$_3$ (known) | 0.1<br>0.01 | 40<br>0 |
| (8) (C$_2$H$_5$O)$_2$P(S)-N...; C$_2$H$_5$O, CH$_3$S-P(S)-O-... CH$_3$ | 0.1<br>0.01 | 100<br>60 |
| (2) (C$_2$H$_5$O)$_2$P(S)-N...; C$_2$H$_5$O, n-C$_3$H$_7$S-P(S)-O-... CH$_3$ | 0.1<br>0.01 | 100<br>99 |
| (15) (C$_2$H$_5$O)$_2$P(S)-N...; C$_2$H$_5$O, n-C$_3$H$_7$S-P(O)-O-... CH$_3$ | 0.1<br>0.01 | 100<br>100 |

Table 2-continued (insects which damage plants)

(*Myzus* test)

| Active compounds | Active compound concentration in % | Degree of destruction in % after 1 day |
|---|---|---|
| Compound (3): $(C_2H_5O)_2P(=S)-N$ pyrazole ring with $-O-P(=S)(S-n-C_3H_7)_2$ and $CH_3$ | 0.1<br>0.01 | 100<br>75 |
| Compound (7): $(C_2H_5O)_2P(=S)-N$ pyrazole with $-O-P(=S)(S-n-C_3H_7)(O-n-C_3H_7)$ and $CH_3$ | 0.1<br>0.01 | 100<br>90 |
| Compound (12): $(C_2H_5O)_2P(=S)-N$ pyrazole with $-O-P(=S)(S-n-C_3H_7)(NH-CH_3)$ and $CH_3$ | 0.1<br>0.01 | 100<br>98 |
| Compound (14): $n-C_3H_7S-P(=S)(OC_2H_5)-N$ pyrazole with $-O-P(=O)(OC_2H_5)_2$ and $CH_3$ | 0.1<br>0.01 | 100<br>100 |
| Compound (1): $n-C_3H_7S-P(=S)(OC_2H_5)-N$ pyrazole with $-O-P(=S)(OC_2H_5)_2$ and $CH_3$ | 0.1<br>0.01 | 100<br>99 |
| Compound (13): $n-C_3H_7S-P(=S)(OC_2H_5)-N$ pyrazole with $-O-P(=S)(OC_2H_5)(C_2H_5)$ and $CH_3$ | 0.1<br>0.01 | 100<br>100 |
| Compound (16): $n-C_3H_7S-P(=S)(OC_2H_5)-N$ pyrazole with $-O-P(=S)(OC_2H_5)(NH-iso-C_3H_7)$ and $CH_3$ | 0.1<br>0.01 | 100<br>50 |

Table 2-continued

| | (insects which damage plants) (Myzus test) | |
|---|---|---|
| Active compounds | Active compound concentration in % | Degree of destruction in % after 1 day |
| 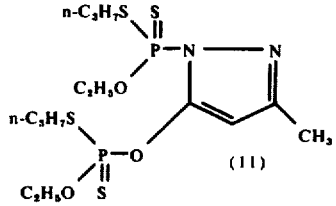 (11) | 0.1<br>0.01 | 100<br>100 |
| 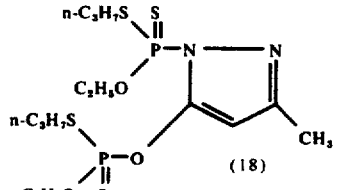 (18) | 0.1<br>0.01 | 100<br>50 |
| 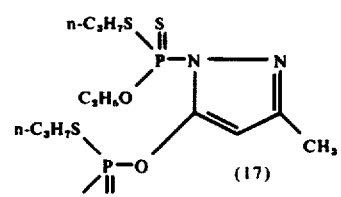 (17) | 0.1<br>0.01 | 100<br>60 |

EXAMPLE 3

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 3

| | (mites which damage plants) (Tetranychus test) | |
|---|---|---|
| Active compounds | Active compound concentration in % | Degree of destruction in % after 2 days |
| 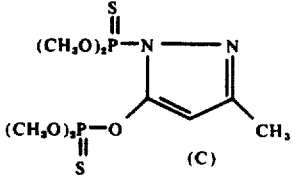 (C) (known) | 0.1 | 0 |

Table 3-continued (mites which damage plants)
(Tetranychus test)

| Active compounds | Active compound concentration in % | Degree of destruction in % after 2 days |
|---|---|---|
| (F) (known) | 0.1 | 0 |
| (2) | 0.1 | 99 |
| (15) | 0.1 | 100 |
| (12) | 0.1 | 98 |
| (14) | 0.1 | 98 |
| (1) | 0.1 | 98 |
| (13) | 0.1 | 98 |

Table 3-continued (mites which damage plants)
(*Tetranychus* test)

| Active compounds | Active compound concentration in % | Degree of destruction in % after 2 days |
|---|---|---|
| 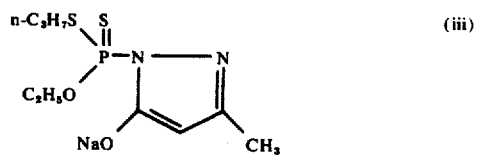 (16) | 0.1 | 95 |
| 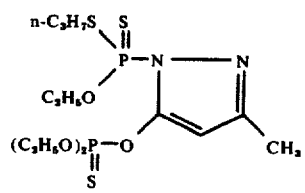 (11) | 0.1 | 98 |

The process of the present invention is illustrated by the following preparative Examples:

EXAMPLE 4 a. The sodium salt of 1-(ethoxy-n-propylthio-thiono-phosphoryl)-3-methyl-5-hydroxypyrazole, which was required as a starting material and has not previously been described in the literature, could be obtained, for example, as follows:

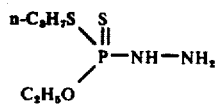 (i)

219 g of O-ethyl-S-n-propylthionothiolphosphoric acid diester chloride were added to 180 ml of hydrazine hydrate at 5 to 10° C and the mixture was stirred for 1 hour, after which 800 ml of chloroform were added. The organic phase was separated off, washed twice with water and dried and the solvent was distilled off. After subjecting the residue to "slight distillation", 184 g (86% of theory) of O-ethyl- S-n-propyl-thionothiolphosphoric acid diester hydrazide having a refractive index $n_D^{23}$ of 1.5492 were obtained.

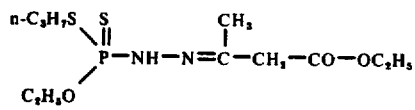 (ii)

130 g of ethyl acetoacetate were added over the course of one hour to 214 g of the product prepared according to (i), dissolved in 600 ml of toluene, during which addition the temperature of the mixture rose to 45° C. The water produced could be bound by adding sodium sulfate. The reaction mixture was stirred for a further 3 hours and was filtered, and the solvent was then evaporated off. The residue was subjected to "slight distillation". 242 g (93% of theory) of O,O-diethylthionophosphorylhydrazono-acetoacetic acid ethyl ester having a refractive index $n_D^{23}$ of 1.5260 were thus obtained.

(iii)

A 1 molar solution of sodium ethylate was added to 326 g (1 mole) of the substance obtained according to (ii), in 1,000 ml of ether, during which addition the temperature of the mixture rose by 15° C. The reaction mixture was stirred for 24 hours and the precipitate which had separated out was filtered off, washed with ether and dried on clay. 200 g (73% of theory) of the compound of the above formula, having a melting point of 168° C, were obtained.

b)

(1)

19 g (0.1 mole) of O,O-diethylthionophosphoric acid diester chloride were added dropwise to a solution of 30 g (0.1 mole) of the sodium salt of 1-(ethoxy-n-propylthio-thionophosphoryl) -3-methyl-5-hydroxy-pyrazole in 200 ml of acetonitrile. The reaction was then stirred for 3 hours at 60° C, and after having cooled, was poured into water. After extracting the aqueous solution by shaking with methylene chloride, the organic phase was washed twice with water and dried, the solvent was removed under reduced pressure and the residue was subjected to "slight distillation". 40 g (93% of theory) of O,O-diethyl-O-[1-(ethoxy-n-propylthiothiono-phosphoryl) -3-methyl-pyrazol(-5)yl]-thionophosphoric acid ester having a refractive index $n_D^{25}$ of 1.5319 were obtained.

The following compounds of the general formula

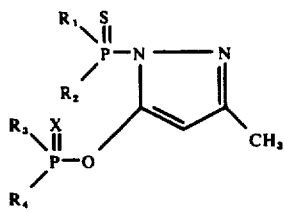

(I)

could be prepared analogously:

Table 4

| Compound No. | $R_1$ | $R_2$ | $R_3$ | $R_4$ | X | Yield (% of theory) | Physical data (melting point °C: refractive index) |
|---|---|---|---|---|---|---|---|
| 2 | $C_2H_5O-$ | $C_2H_5O-$ | $n-C_3H_7S-$ | $C_2H_5O-$ | S | 87 | $n_D^{22}$ : 1.5338 |
| 3 | $C_2H_5O-$ | $C_2H_5O-$ | $n-C_3H_7S-$ | $n-C_3H_7S-$ | S | 89 | $n_D^{20}$ : 1.5570 |
| 4 | $C_2H_5O-$ | $C_2H_5O-$ | $C_2H_5S-$ | $n-C_3H_7O-$ | S | 83 | $n_D^{25}$ : 1.5330 |
| 5 | $C_2H_5O-$ | $C_2H_5O-$ | $CH_3S-$ | $n-C_3H_7O-$ | S | 86 | $n_D^{25}$ : 1.5370 |
| 6 | $C_2H_5O-$ | $C_2H_5O-$ | $CH_3S-$ | $iso-C_3H_7O-$ | S | 86 | $n_D^{25}$ : 1.5341 |
| 7 | $C_2H_5O-$ | $C_2H_5O-$ | $n-C_3H_7S-$ | $n-C_3H_7O-$ | S | 92 | $n_D^{25}$ : 1.5294 |
| 8 | $C_2H_5O-$ | $C_2H_5O-$ | $C_2H_5O-$ | $CH_3S-$ | S | 84 | $n_D^{25}$ : 1.5341 |
| 9 | $C_2H_5O-$ | $C_2H_5O-$ | $n-C_4H_9S-$ | $iso-C_3H_7O-$ | S | 82 | $n_D^{25}$ : 1.5304 |
| 10 | $C_2H_5O-$ | $C_2H_5O-$ | $n-C_3H_7S-$ | $iso-C_3H_7O-$ | S | 92 | $n_D^{25}$ : 1.5364 |
| 11 | $C_2H_5O-$ | $n-C_3H_7S-$ | $C_2H_5O-$ | $n-C_3H_7S-$ | S | 69 | $n_D^{20}$ : 1.5460 |
| 12 | $C_2H_5O-$ | $C_2H_5O-$ | $n-C_3H_7S-$ | $CH_3-NH-$ | S | 79 | $n_D^{25}$ : 1.5491 |
| 13 | $C_2H_5O-$ | $n-C_3H_7S-$ | $C_2H_5O-$ | $C_2H_5-$ | S | 84 | $n_D^{25}$ : 1.5439 |
| 14 | $C_2H_5O-$ | $n-C_3H_7S-$ | $C_2H_5O-$ | $C_2H_5O-$ | O | 84 | $n_D^{20}$ : 1.5135 |
| 15 | $C_2H_5O-$ | $C_2H_5O-$ | $n-C_3H_7S-$ | $C_2H_5O-$ | O | 89 | $n_D^{22}$ : 1.5096 |
| 16 | $C_2H_5O-$ | $n-C_3H_7S-$ | $C_2H_5O-$ | $iso-C_3H_7-NH-$ | S | 83 | $n_D^{25}$ : 1.5418 |
| 17 | $C_2H_5O-$ | $n-C_3H_7S-$ | $n-C_3H_7S-$ | $iso-C_3H_7O-$ | S | 78 | $n_D^{25}$ : 1.5572 |
| 18 | $C_2H_5O-$ | $n-C_3H_7S-$ | $n-C_3H_7S-$ | $n-C_3H_7O-$ | S | 78 | $n_D^{25}$ : 1.5538 |
| 19 | $C_2H_5O-$ | $n-C_3H_7S-$ | $n-C_4H_9S-$ | $iso-C_3H_7O-$ | S | 80 | $n_D^{25}$ : 1.5510 |

It will be appreciated that the instant specification and examples are set forth by way of illustration and not limitation, and that various modifications and changes may be made without departing from the spirit and scope of the present invention.

What is claimed is:

1. A diphosphorylated pyrazole of the formula

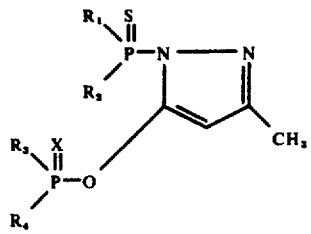

in which
$R_1$ is alkoxy with 1 to 4 carbon atoms,
$R_2$ and $R_3$ each independently is alkoxy or alkylthio with 1 to 6 carbon atoms,
$R_4$ is alkoxy, alkylthio, alkylamino or alkyl with 1 to 5 carbon atoms, provided that at least one of the radicals $R_2$, $R_3$ and $R_4$ is alkylthio, and X is oxygen or sulfur.

2. A compound according to claim 1, in which $R_1$ is alkoxy with 1 to 3 carbon atoms, $R_2$ is alkoxy with 1 to 3 carbon atoms, or alkylthio with 1 to 4 carbon atoms, $R_3$ is alkoxy with 1 to 3 carbon atoms or alkylthio with 1 to 5 carbon atoms, $R_4$ is alkyl with 1 to 3 carbon atoms or alkoxy, alkylthio or alkylamino each with 1 to 4 carbon atoms, provided that at least one of the radicals $R_2$, $R_3$ and $R_4$ is alkylthio, and X is sulfur.

3. The compound according to claim 1 wherein such compound is O,O-diethyl-O-[1-(ethoxy-n-propylthi- othionophosphoryl)- 3-methyl-pyrazol(5)yl]-thionophosphoric acid ester of the formula

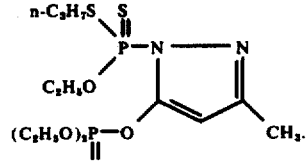

4. The compound according to claim 1 wherein such compound is O-ethyl-S-n-propyl-O-[1-(diethoxythionophosphoryl)- 3-methyl-pyrazol(5)yl]-thionothiolphosphoric acid ester of the formula

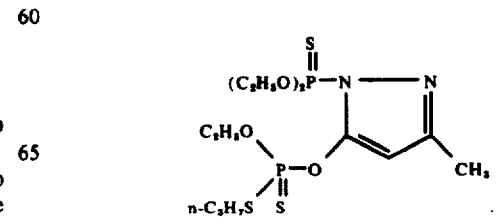

5. The compound according to claim 1 wherein such compound is N-methyl-S-n-propyl-[1-(diethoxythionophosphoryl)-3- methyl-pyrazol(5)yl]-thionothiolphosphoric acid ester amide of the formula

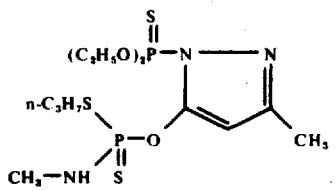

6. The compound according to claim 1 wherein such compound is O,O-diethyl-O-[1-(ethoxy-n-propylthiothionophosphoryl)- 3-methyl-pyrazol(5)yl]-phosphoric acid ester of the formula

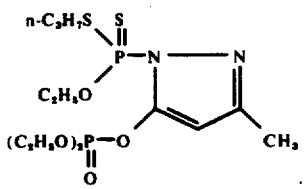

7. The compound according to claim 1 wherein such compound is O-ethyl-S-n-propyl-O-[1-(diethoxythionophosphoryl)- 3-methyl-pyrazol(5)yl]-thiolphosphoric acid ester of the formula

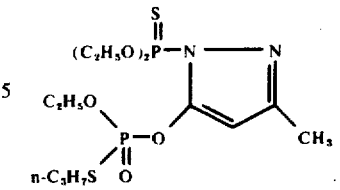

8. An arthropodicidal composition containing as active ingredient an arthropodicidally effective amount of a compound according to claim 1 in admixture with a diluent.

9. A method of combating arthropods, which comprises applying to the arthropods, or to habitat thereof, an arthropodicidally effective amount of a compound according to claim 1.

10. The method according to claim 9 in which said compound is

O,O-diethyl-O-[1-(ethoxy-n-propylthiothionophosphoryl)- 3-methyl-pyrazol(5)yl]-thionophosphoric acid ester, O-ethyl-S-n-propyl-O-[1-(diethoxythionophosphoryl)-3- methyl-pyrazol(5)yl]-thionothiolphosphoric acid ester, N-methyl-S-n-propyl-[1-(diethoxythionophosphoryl)-3- methyl-pyrazol (5)yl]-thionothiolphosphoric acid ester, O,O-diethyl-O-[1-(ethoxy-n-propylthiothionophosphoryl)- 3-methyl-pyrazol(5)yl]-phosphoric acid ester, or O-ethyl-S-n-propyl-O-[1-(diethoxythionophosphoryl)-3- methyl-pryazol(5)yl]-thiolposphoric acid ester.

* * * * *